United States Patent [19]

Hakomori

[11] Patent Number: 5,308,614
[45] Date of Patent: May 3, 1994

[54] METHODS FOR THE PRODUCTION OF ANTIBODIES AND INDUCTION OF IMMUNE RESPONSES TO TUMOR-ASSOCIATED GANGLIOSIDES BY IMMUNIZATION WITH GANGLIOSIDE LACTONES

[75] Inventor: Sen-itiroh Hakomori, Mercer Island, Wash.

[73] Assignee: The Biomembrane Institute, Seattle, Wash.

[21] Appl. No.: 996,509

[22] Filed: Dec. 21, 1992

Related U.S. Application Data

[63] Continuation of Ser. No. 173,962, Mar. 28, 1988.

[51] Int. Cl.$^5$ ............... A61K 31/70; A61K 37/00; A61K 39/00
[52] U.S. Cl. ................ 424/88; 424/93 U; 514/23; 514/42; 514/54; 436/519; 436/524
[58] Field of Search ............ 424/85.8, 88, 93 U; 436/519, 524; 514/23, 42, 54

[56] References Cited
PUBLICATIONS

Nores et al. Journal of Immunology vol. 139 3171-3176 Dec. 1, 1987.
Livingston et al. P.N.A.S. vol. 84 pp. 2911-2915 May 1987.
Pukel, C. S. et al. J. Exp. med. 155:1133-1147 (1982), "GD3, a prominent ganglioside of human melanoma."
Ravindramath, M. H. et al., Int'l Rev. Immunol. 7:303-329 (1991, "Rule of gangliosides in active immunotherapy with melanoma vaccine."
Dialog Acc. No. 109048445, Edwards, et al.
Dialog Acc. No. 102132016. Szent-Gyorghi, et al.
Dialog Acc. No. 6544639. Roberts, et al.
Dialog Acc. No. 6457488. Tham, et al.
Dialog Acc. No. 5741651. Jiang, et al.
Weir, et al. Handbook of Immunol. 1973. pp. 1.1-1.3. Blackwell Sci. Pub.

*Primary Examiner*—Christine M. Nucker
*Assistant Examiner*—T. Cunningham
*Attorney, Agent, or Firm*—Sughrue, Mion, Zinn, Macpeak & Seas

[57] ABSTRACT

The present invention relates to an improved method for the production of antibodies to tumor-associated gangliosides using ganglioside lactones. The resulting antibodies are useful in the detection and treatment of tumors containing gangliosides. The present invention also relates to methods of treatment of tumors by active immunization using ganglioside lactones.

5 Claims, 3 Drawing Sheets

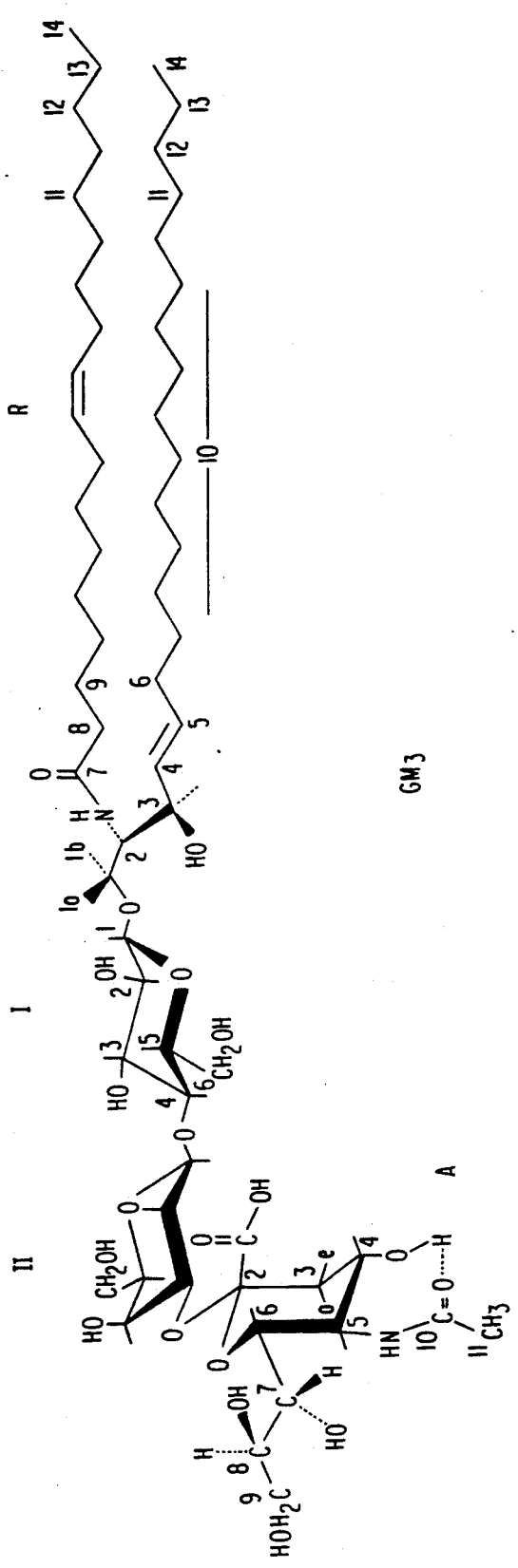
FIG.1A GM3
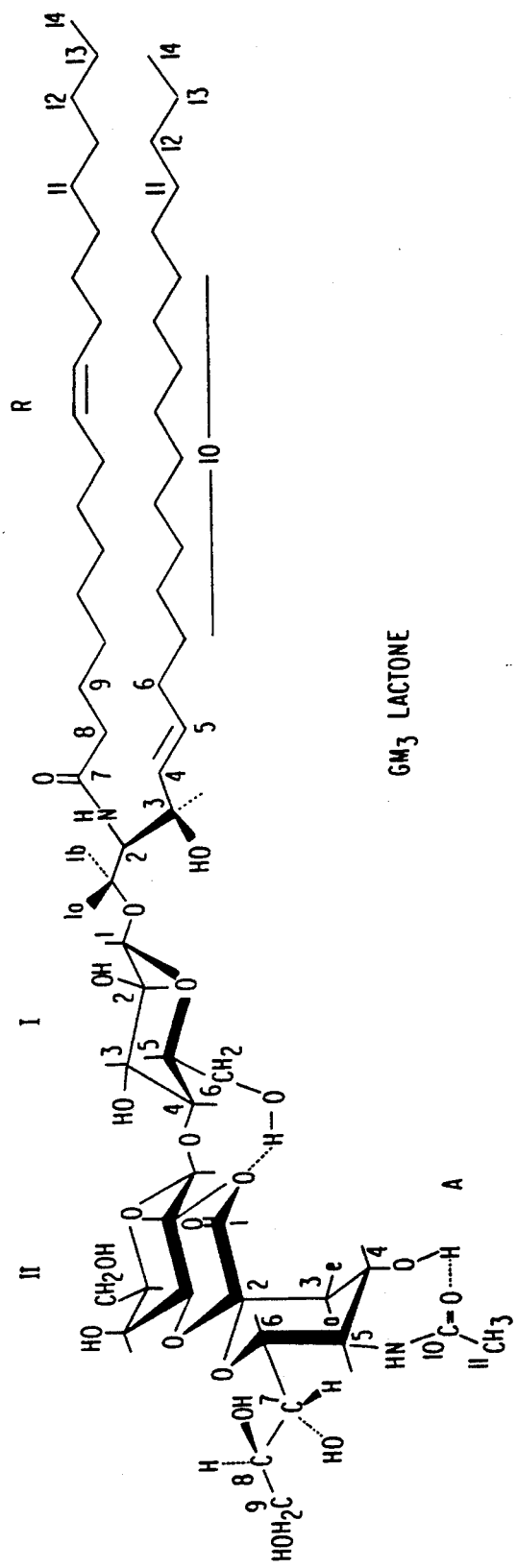
FIG.1B GM3 LACTONE

METHODS FOR THE PRODUCTION OF ANTIBODIES AND INDUCTION OF IMMUNE RESPONSES TO TUMOR-ASSOCIATED GANGLIOSIDES BY IMMUNIZATION WITH GANGLIOSIDE LACTONES

This is a continuation of application Ser. No. 07/173962 filed Mar. 28, 1988.

FIELD OF THE INVENTION

The present invention relates to an improved method for the production of antibodies to tumor-associated gangliosides using ganglioside lactones. The resulting antibodies are useful in the detection and treatment of tumors containing gangliosides. The present invention also relates to methods of treatment of tumors by active immunization using ganglioside lactones.

BACKGROUND OF THE INVENTION

Cells are surrounded by plasma membranes. Plasma membranes contain components called glycosphingolipids inserted therein which aide in the formation of the characteristic surface structure of the cells. Each type of cell is characterized by a specific profile of the glycosphingolipid components. including those components known as gangliosides. located in its plasma membrane. Gangliosides contain a particular type of acidic carbohydrate known as sialic acid. Further, many specific types of cells, including tumor cells, are characterized by the presence of a particular type of ganglioside located in their plasma membranes.

In recent years, a number of monoclonal antibodies have been established after immunization with human tumor cells or tissues. These monoclonal antibodies were selected by their positive reactivity to tumor cells and negative reactivity to normal cells or tissues. Many of the monoclonal antibodies selected by preferential reactivity to melanomas, neuroblastomas and adenocarcinomas have been identified as being directed to gangliosides. Some of these anti-ganglioside antibodies with specific isotypes (particularly IgG$_3$ and IgG$_{2a}$) and which show strong reactivity to gangliosides have been found to suppress tumor growth in vivo. For example, melanomas of some patients have been found to regress following a large dose administration of a specific anti-GD$_3$ ganglioside antibody (Houghton, A. N. et al, *Proc. Natl. Acad. Sci. USA*, 82:1242–1246 (1985)). Further, recently it has been demonstrated that GM$_2$ absorbed on BCG bacteria showed a detectable immune response. Thus, it has been asserted that GM$_2$ could be a useful vaccine for human melanomas (Livingston, P.O. et al, *Proc. Natl. Acad. Sci. USA.* 84:2911–2915 (1987). Hence, gangliosides are important antigens and immunogens of tumor tissues and cells (Hakomori, S., *Annu. Rev. Immunol.*, 2:103–126 (1984); Hakomori, S., In *Handbook of Lipid Research*. Volume 3, *Sphingolipid Biochemistry*, Kanfer, J. N. et al Eds., Plenum, New York, pages 1–165 (1983); and Hakomori, S., *Sci. Amer.*, 254:44–53 (1986)).

However, the use of tumor cells (including cell membranes), tumor tissues, or isolated gangliosides absorbed on bacteria as immunogens, is extremely laborious and requires extensive selection studies. In addition, although gangliosides are important cell type-specific markers, they are poor immunogens in eliciting humoral or cellular immune responses. As a result, repeated immunization with tumor cells (including cell membranes), tumor tissues or isolated gangliosides absorbed on bacteria or other carriers is disadvantageously necessary.

A small portion of gangliosides are present in tumor cells and tissues in the form of a lactone thereof. For example, less than 0.1% of the particular ganglioside, designated GM$_3$ (see FIG. 1A), present in melanoma cells has been identified as a lactone thereof (see FIG. 1B). Ganglioside lactones are defined as the inner ester between the carboxyl group of the sialic acid and the primary or secondary hydroxyl group of the sugar residues within the same molecule. One example of a GM$_3$ lactone, wherein the carboxyl group of sialic acid is esterified with the C-2 secondary hydroxyl group of the penultimate galactose is shown in FIG. 1B (Yu, R. K. et al, *J. Biochem. Tokyo*, 98:1307 (1985)). This structure is sterically stable and relatively stable at acidic to neutral pH, although unstable at alkaline pH. While galactoside lactones have been detected and believed to be naturally occurring plasma membrane components, their quantity is extremely low and thus their natural occurrence has been disputed (Nores. G. A. et al, *J. Immunol.*, 139:3171–3176 (1987) and Riboni. L., *J. Biol. Chem.*, 261:8514–8519 (1986)).

Despite the question about their natural occurrence, it has been demonstrated in the present invention that ganglioside lactones are strong immunogens, which can cause a much greater immune response than native gangliosides. Further, it has been found in the present invention that the antibodies produced using ganglioside lactones as immunogens are of the IgG$_3$ isotype, which is extremely useful compared to antibodies of the IgM isotype produced using native gangliosides, (i) in detecting tumors containing gangliosides, (ii) in suppressing growth of tumors containing gangliosides in vitro and in vivo and (iii) in inducing antibody-dependent cytotoxicity in vivo. In addition, it has been found in the present invention that ganglioside lactones themselves are effective for suppressing growth of tumors containing gangliosides in vivo, whereas such suppression is not achieved using native gangliosides.

SUMMARY OF THE INVENTION

Accordingly an object of the present invention is to provide a method for the production of antibodies to tumor-associated gangliosides.

Another object of the present invention is to provide a passive immunization method for treating tumors containing gangliosides.

Still another object of the present invention is to provide an active immunization method for treating tumors containing gangliosides.

Yet another object of the present invention is to provide a method for detecting tumors containing gangliosides.

These and other objects of the present invention, which will be apparent from the detailed description of the invention provided hereinafter, have been met by the following embodiments.

In one embodiment, the present invention relates to a method for the production of antibodies to tumor-associated gangliosides comprising:

(1) immunizing an animal with an immunogenic effective amount of a lactone of a tumor-associated ganglioside and a pharmaceutically acceptable carrier;

(2) isolating the immunized cells from said animal;

(3) fusing the isolated immunized cells with myeloma cells; and
(4) screening for hybridomas which produce antibodies having binding specificity to said ganglioside and collecting the antibodies so produced.

In a second embodiment, the present invention relates to a passive immunization method for treating tumors containing gangliosides comprising administering to a subject:
(A) a pharmaceutically effective amount of an antibody produced by the process comprising:
(1) immunizing an animal with an immunogenic effective amount of a lactone of a tumor-associated ganglioside and a pharmaceutically acceptable carrier;
(2) isolating the immunized cells from said animal;
(3) fusing the isolated immunized cells with myeloma cells; and
(4) screening for hybridomas which produce antibodies having binding specificity to said ganglioside and collecting the antibodies so produced; and
(B) a pharmaceutically acceptable carrier.

In a third embodiment, the present invention relates to an active immunization method for treating tumors containing gangliosides comprising administering to a subject:
(A) an immunogenic effective amount of a lactone of a tumor-associated ganglioside; and
(B) a pharmaceutically acceptable carrier.

In a fourth embodiment, the present invention relates to a method for detecting tumors containing gangliosides comprising:
(A) contacting a test sample with an antibody produced by the process comprising:
(1) immunizing an animal with an immunogenic effective amount of a lactone of a tumor-associated ganglioside and a pharmaceutically acceptable carrier;
(2) isolating the immunized cells from said animal;
(3) fusing the isolated immunized cells with myeloma cells;
(4) screening for hybridomas which produce antibodies having binding specificity to said ganglioside and collecting the antibodies so produced; and
(B) assaying for specific binding of said antibody to antigen in said test sample.

BRIEF DESCRIPTION OF THE DRAWINGS

FIG. 1A illustrates the structure of $GM_3$. FIG. 1B illustrates the structure of $GM_3$ lactone. The carboxyl group (COOH) in FIG. 1A and the hydroxyl group at the C-2 position of the galactose (residue II) are esterified to form a six-member ring between the galactose (residue II) and sialic acid (residue A) to give rise to the structure of the $GM_3$ lactone shown in FIG. 1B. In FIGS. 1A and 1B, residue I and residue R are glucose and ceramide, respectively.

Figure 2A:
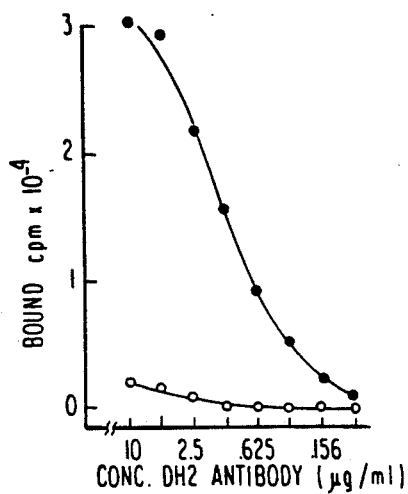
FIG. 2A shows the reactivity of DH2 antibody with $GM_3$ (·) or $GM_3$ lactone (○). as determined in a solid-phase radioimmunoassay, which was carried out by dissolving the gangliosides together with phosphatidylcholine (hereinafter "PC") and cholesterol in ethanol and drying on polyvinyl plastic plates.
Figure 2B:
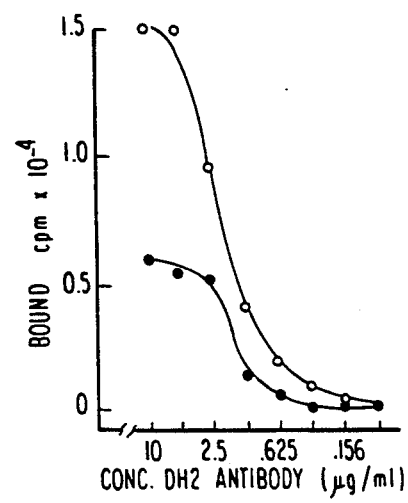
FIG. 2B shows the reactivity of DH2 antibody with $GM_3$ (·) or $GM_3$ lactone (○) as determined in a solid-phase radioimmunoassay, which was carried out in gelatin-coated polyvinyl plastic plates on which an aqueous solution of $GM_3$ or $GM_3$ lactone was added and incubated to ensure adsorption of such to the gelatin coat. The aqueous solution is made in phosphate buffered saline (hereinafter "PBS").

The data in FIGS. 2A and 2B is the average of triplicate experiments. Note, as shown in FIG. 2B, $GM_3$ lactone reactivity of DH2 antibody can be specifically detected when adsorbed on gelatin-coated polyvinyl plastic plates.

Figure 3:
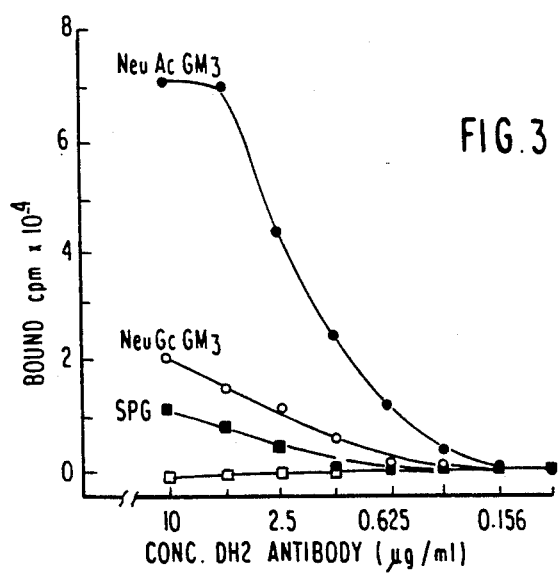

FIG. 3 illustrates the reactivity of DH2 antibody with the following glycolipids: NeuAcGM$_3$ (·); NeuGcGM$_3$ (○): sialylparagloboside ( ); or other glycolipids, $GM_1$, GD1a, GD1b, GT1, galactosylceramide and sialyllactonorhexaosylceramide (all indicated as □), as determined in a solid-phase radioimmunoassay, which was carried out by dissolving the glycolipids together with PC and cholesterol in ethanol and drying in polyvinyl plastic plates. The data in FIG. 3 is the average of triplicate experiments.

Figure 4:
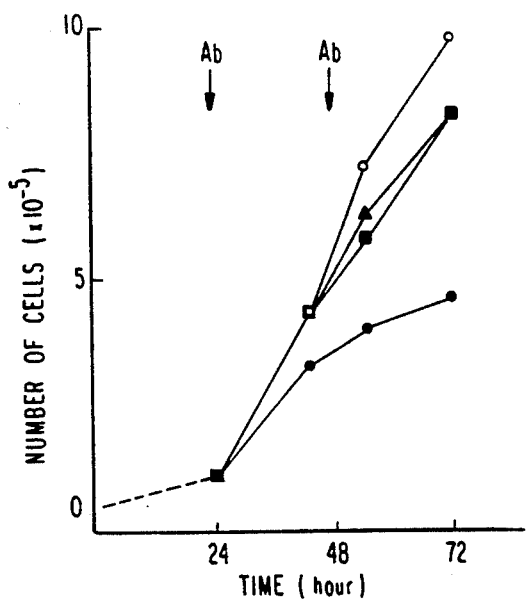

FIG. 4 illustrates the inhibition of B16 melanoma cell growth in vitro by the following antibodies: DH2 (·); M2590 ( ); Cu-1 anti-Tn ( ); and PBS as a control (○). In FIG. 4, each data point represents the average of triplicate experiments. The standard deviation was less than 15%.

Figure 5:
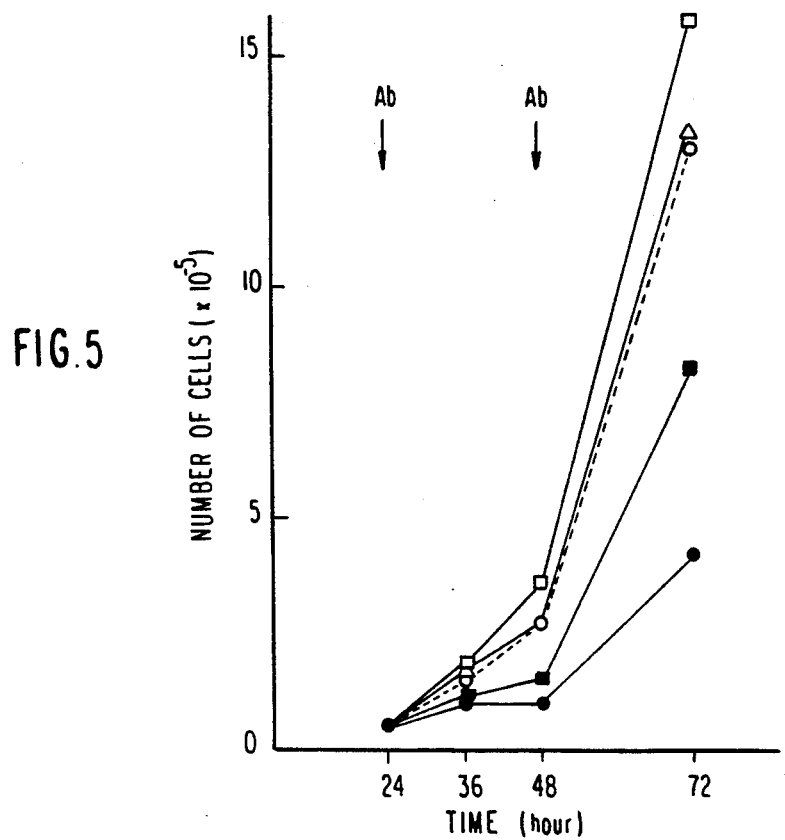

FIG. 5 illustrates the effects of the following concentrations of DH2 antibody on B16 melanoma cell growth in vitro: 100 μg/ml (·); 50 μg/ml ( ); 25 μg/ml (○); and 12.5 μg/ml (Δ); and PBS as a control (□). In FIG. 5, each data point represents the average of triplicate experiments. The standard deviation was less than 15%.

Figure 6A:
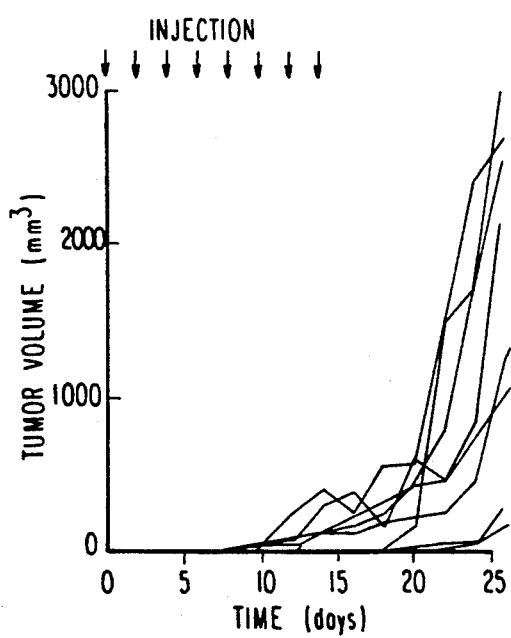
Figure 6B:
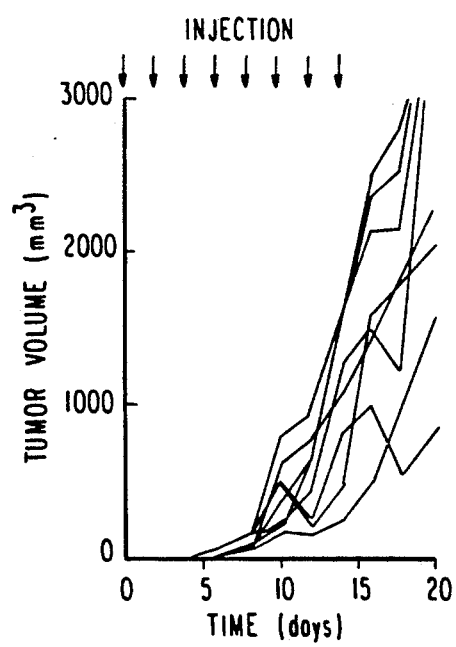

FIG. 6A illustrates the effect of DH2 antibody on B16 melanoma growth in vivo. FIG. 6B illustrates the effect of PBS as a control on B16 melanoma growth in vivo.

DETAILED DESCRIPTION OF THE INVENTION

As discussed above, in one embodiment, the present invention relates to a method for the production of antibodies to tumor-associated gangliosides comprising:
(1) immunizing an animal with an immunogenic effective amount of a lactone of a tumor-associated ganglioside and a pharmaceutically acceptable carrier;
(2) isolating the immunized cells from said animal;
(3) fusing the isolated immunized cells with myeloma cells; and
(4) screening for hybridomas which produce antibodies having binding specificity to said ganglioside and collecting the antibodies so produced.

In a second embodiment, the present invention relates to a passive immunization method for treating tumors containing gangliosides comprising administering to a subject:
(A) a pharmaceutically effective amount of an antibody produced by the process comprising:
(1) immunizing an animal with an immunogenic effective amount of a lactone of a tumor-associated ganglioside and a pharmaceutically acceptable carrier;
(2) isolating the immunized cells from said animal;
(3) fusing the isolated immunized cells with myeloma cells; and
(4) screening for hybridomas which produce antibodies having binding specificity to said ganglioside and collecting the antibodies so produced; and (B) a pharmaceutically acceptable carrier In a third embodiment, the present invention relates to an active immunization method for treating tumors containing gangliosides comprising administering to a subject:
(A) an immunogenic effective amount of a lactone of a tumor-associated ganglioside; and
(B) a pharmaceutically acceptable carrier.

In a fourth embodiment the present invention relates to a method for detecting tumors containing gangliosides comprising:
(A) contacting a test sample with an antibody produced by the process comprising:
(1) immunizing an animal with an immunogenic effective amount of a lactone of a tumor-associated ganglioside and a pharmaceutically acceptable carrier;
(2) isolating the immunized cells from said animal;
(3) fusing the isolated immunized cells with myeloma cells;
(4) screening for hybridomas which produce antibodies having binding specificity to said ganglioside and collecting the antibodies so produced; and
(B) assaying for specific binding of said antibody to antigen in said test sample.

The particular tumor-associated ganglioside employed in the present invention is not critical thereto. Examples of such tumor-associated gangliosides include $GD_3$ found in melanomas (Pukel, C. S. et al, *J. Exp. Med.*, 155:1133–1147 (1982) and Nudelman, E. et al, *J. Biol. Chem.*, 257:12752–12756 (1982)): $GD_2$ found in melanomas and neuroectodermal tumors such as neuroblastomas (Cahan, L. et al, *Proc. Natl. Acad. Sci. USA*, 79:7629–7633 (1982)); sialyl Le$^a$ found in gastrointestinal and pancreatic cancers (Magnani, J. L. et al, *J. Biol. Chem.*, 257:14365–14369 (1982)); sialyl Le$^X$ found in colorectal, gastrointestinal and lung adenocarcinomas (Fukushima, K. et al, *Cancer Res.*, 44:5279–5285 (1984)); sialyl difucosyl Le$^x$ found in colorectal, gastrointestinal and lung adenocarcinomas (Fukushi, Y. et al, *J. Biol. Chem.*, 259:10511–10517 (1984)); $GM_3$ found in melanomas (Taniguchi, M., *Gann*, 75:418–426 (1984); Hirabayashi, Y. et al, *J. Biol. Chem.*, 260:13328–13333 (1985); Nores. G. et al, *J. Immunol.*, 139:3171–3176 (1987); 6C ganglioside found in colorectal carcinomas (Hakomori, S. et al, *Biochem. Biophys. Res. Commun.*, 113:791–798 (1983); G2 ganglioside found in myelogeneous leukemia cells (Fukuda, Y. et al, *J. Biol. Chem.*, 260:1060–1082 (1985); disialosyl Le$^a$ found in colorectal cancers (Nudelman, E. et al, *J. Biol. Chem.*, 261:5487–5495 (1986); monosialyl type 1 chain found in colorectal carcinomas and teratocarcinomas (Nilsson, O. et al, *FEBS Letters*, 182:398–402 (1985); Fakuda, M. N. et al, *J. Biol. Chem.*, 261:5145–5153 (1986): disialosyl type 1 chain found in colorectal cancers (Fukushi. Y. et al. *Biochem.*, 25:2859–2866 (1986); and fucosyl $GM_1$ found in small cell lung carcinomas (Nilsson, O. et al. *Glycoconjugate J.*, 1:43–49 (1984)).

Lactones of the gangliosides can be prepared by dissolving any ganglioside in glacial acetic acid and allowing the solution to stand for at least 48 hours, followed by lyophilization of the acetic acid. Formation of the ganglioside lactones can be monitored by thin layer chromatography, using high performance thin layer chromatography plates obtained from J. T. Baker Chemical Co (Phillipsburg, N.J.) and chloroform:methanol:water (50:40:10 (v/v/v)) containing 0.05% (w/v) $CaCl_2$ as a solvent since ganglioside lactones show a distinctively higher mobility than native gangliosides on thin layer chromatography. Note, the above solvent composition is not critical and any well known solvent which can separate gangliosides from the lactones thereof can be employed, for example, as described in Nores, G. A. et al. *J. Immunol.* 139:3171–3176 (1987).

Alternatively, and more efficiently ganglioside lactones can be prepared by dissolving any ganglioside in chloroform:methanol:12N HCl (10:35:4.5 (v/v/v)) and allowing the solution to stand for about one day. The resulting solution is then chromatographed using DEAE-Sephadex in chloroform:methanol:water (0.1:1:1 (v/v/v)). Two main components and several minor components, the structures of the latter remain to be elucidated, are resolvable in this system. The resulting ganglioside lactones can be purified by HPLC on Iatrobeads 6RS8010 in isopropanol:hexane:water (55:25:20 (v/v/v)) with gradient elution being carried out as described by Watanabe, K. et al, *J. Lipid Res.*, 22:1020–1024 (1981). The structure of the purified ganglioside lactones can be verified by direct probe fast atom bombardment mass spectrometry as described in Riboni, L., *J. Biol. Chem.*, 261:8514–8519 (1986).

The particular pharmaceutically acceptable carrier to be used along with the lactone of the tumor-associated ganglioside is not critical to the present invention. Examples of such pharmaceutically acceptable carriers include Bacillus Calmette-Guerin (BCG), diptheria toxoid and tetnus toxoid.

Further, the particular pharmaceutically acceptable carrier to be used along with the antibody produced using the lactones of the tumor-associated gangliosides of the present invention is not critical thereto. Examples of such pharmaceutically acceptable carriers include Bacillus Calmette-Guerin (BCG). diptheria toxoid and tetanus toxoid.

In addition, lactones of tumor-associated gangliosides as immunogens when appropriately assembled in either natural or artificial membranes can be useful as anti-tumor vaccines (Livingston, P.O. et al. *Proc. Natl. Acad, Sci. USA*, 84:2911–2915 (1987); and Livingston. P.O. et al, *J. Immunol.*, 131:2601–2605 (1983)). Another possible carrier would be a *Vaccinia* virus in which a specific ganglioside lactone could be assembled (Stott, E. J., *J. Biol.*, 61:3855–3861 (1987); and Hu, S.-L. et al, *J. Biol.*, 62:176–180 (1988)).

A pharmaceutically acceptable diluent can also be employed in the present invention. The particular pharmaceutically acceptable diluent employed is not critical thereto. Examples of such diluents include physiological saline, Ringer's solution vitamin cocktail and amino acid vitamin cocktail. These diluents can be employed for administering either the lactone of the tumor-associated ganglioside or the antibody having binding specificity thereto.

The lactones of tumor-associated gangliosides may be administered using any of the following modes of administration: intradermal, subcutaneously or intraperitoneal.

The antibodies specific to the tumor-associated gangliosides may be administered intravenously.

The particular animal being immunized with the lactone of the tumor-associated ganglioside is not critical to the present invention. Examples of such animals include mice, rabbits, rats, goats and humans.

As used herein "immunized cells" refers to the sensitized spleen cells of the immunized animal, e.g., those of mice such as Balb/c mice.

The particular myeloma cells employed in the present invention are not critical thereto and can be any well known myeloma cell useful for preparing hybridomas of mouse, rat, rabbit, goat and human origin. Examples of such myeloma cells include HAT sensitive mice myeloma cells such as NS/1 cells and SP-2 cells.

The immunogenic effective amount of the lactone of the tumor-associated ganglioside to be administered in the present invention will vary depending upon the age, weight, sex and species of the animal to be administered. Generally, the immunogenic effective amount is about 2.0 to 5.0 $\mu g$, adsorbed on about 20 to 100 $\mu g$ of carrier per one injection. Generally, from 5 to 10 injections of the ganglioside lactone are employed but the present invention is not limited thereto.

The pharmaceutically effective amount of the antibodies of the present invention to be administered will vary depending upon the age, weight, sex and species of the animal to be administered. Generally, the pharmaceutically effective amount is about 1.0 to 5.0 $\mu g/100$ g body weight of animal per one injection. Generally, from 5 to 10 injections of the antibodies are employed but the present invention is not limited thereto.

The particular ganglioside lactone or antibody thereto which will be administered will depend upon the particular ganglioside lactone present in the tumor which is intended to be treated. Information as to the particular ganglioside present in the tumor can be obtained by a serum assay or biopsy assay for the various gangliosides. As used herein, "treatment" means both prevention of tumor formation and treatment of existing tumors.

Immunizing the animals, e.g., mice, with the ganglioside lactones of the present invention, isolating the immunized cells fusing the immunized cells with, e.g., mouse myeloma cells, and culturing the resulting fused cells under conditions which allow for growth of hybridomas, are all conducted by methods well known and readily determined in the art (Young. W. W. et al, *J. Exp. Med.*, 150:1008–1019 (1979) and Fukushi, Y. et al, *J. Biol. Chem.*,259:4681–4685 (1984)).

The resulting hybridomas are then screened so as to isolate those which produce monoclonal antibodies having binding specificity to the ganglioside lactones, in for example a solid-phase radioimmunoassay using ganglioside-coated wells and assaying using a second antibody (rabbit anti-mouse IgM+IgG (Miles Biochemical, Elkhart, Ind.)) and $^{125}$I-labeled Protein A as described in more detail hereinafter.

In the method for detecting tumors containing gangliosides of the present invention "test sample" means, for example, tissue biopsies, serum, ascites fluid and spinal fluid.

In this method, detection can occur either in vitro or in vivo. In vitro detection can be carried out using any of the well known in vitro immunological assays, such as those described by Young. W. W. et al, *J. Exp. Med.*, 150:1008–1019 (1979) and Kannagi R. et al, *Cancer Res.*, 43:4997–5005 (1983). Further, in vivo detection can be carried out using any of the well known in vivo immunological assays, such as those described by Burchell, J. et al, *Int. J. Cancer*, 34:763–768 (1984): Epenetos. A. A. et al, *Lancet* 2:999–1004 (1982); Chatal, J.-F. et al, *J. Nuclear Med.*, 25:307–314 (1984); Munz D. L. et al, *J. Nuclear Med.*, 27:1739–1745 (1986); and Keenan, A. N. et al, *J. Nuclear Med.*, 26:531–537 (1985).

The following examples are provided for illustrative purposes only and are in no way intended to limit the scope of the present invention.

EXAMPLE 1

Method of Preparation of Monoclonal Antibodies Using Ganglioside Lactones

A. Production of Monoclonal Antibodies

GM$_3$ was extracted from dog erythrocytes by isopropanol-hexane-water (55:25:20 (v/v/v)) and separated by Folch partition followed by ion exchange chromatography as described in Hakomori. S. In *Handbook of Lipid Research*. Vol. 3, Sphingolipid Biochemistry (Kanfer, J. N. et al, Eds., Plenum, New York, pages 1–165 (1983). Plenum Publishing, New York, pages 1–165 (1983)).

40 $\mu g$ of GM$_3$ or 40 $\mu g$ GM$_3$ lactone, prepared from the resulting GM$_3$ using acetic acid or the chloroform-methanol-HCl method as described above was suspended in 4.0 ml of distilled water, sonicated, and mixed with 1.0 mg of acid-treated *Salmonella minnesota*, as described by Young, W. W. et al, *J. Exp. Med.*, 150:1008–1019 (1979). The *Salmonella minnesota* used was suspended in 1.0% (v/v) aqueous acetic acid and heated for 1 hour at 80° C., followed by dialysis and lyophilization. The suspension was then incubated for 10 min at 37° C. and lyophilized. The lyophilized material was resuspended in 4.0 ml of PBS and aliquots of 2.0 $\mu g$ of GM$_3$ or GM$_3$ lactone on 50 $\mu g$ of *Salmonella minnesota* were injected intravenously weekly into BALB/c mice. A total of 8 injections were made. Three days after the last booster injection, $10^8$ spleen cells from the mice were harvested and fused with $5 \times 10^7$ mouse myeloma SP2 cells as described by Young, W. W. et al, *J. Exp. Med.*, 150:1008–1019 (1979). The resulting hybridomas were grown in RPMI medium supplemented with 10% (v/v) fetal calf serum, as described in detail in Young, W. W. et al, *J. Exp. Med.*, 150:1008–1019 (1979).

The culture supernatants of the resulting hybridomas on the seventh day after fusion were screened on 96-well plastic plates (Becton-Dickinson, Oxnard, Calif.) which had been pre-coated with 0.1% (w/v) gelatin in a solid-phase radioimmunoassay. More specifically, the gelatin-coated plates were incubated with 200 $\mu l$ of 0.1% (w/v) bovine serum albumin for 24 hours at 4° C., washed with PBS once and incubated with 50 $\mu l$ of a 0.2 $\mu$mole/ml GM$_3$ or GM$_3$ lactone in PBS solution overnight at room temperature. The wells were then washed with PBS, and culture supernatants from the hybridomas as the first antibody were added and incubated for 2 hours at room temperature. Then, the first antibody bound to each ganglioside-coated well was assayed using 50 $\mu l$ of a second antibody (rabbit anti-mouse IgM+IgG (Miles Biochemical, Elkhart, Ind.)) and 50 $\mu l$ of $^{125}$I-labeled Protein A to detect binding of the second antibody to the first antibody. Each well was cut and the radioactivity counted in a gamma counter. Only strongly active wells (greater than 2,000 cpm) were regarded as positive. The results are shown in Table I below.

TABLE I

Comparison of Immunogenicity of Native GM₃ and GM₃ Lactone to BALB/c Mice

| | Immunization with: | | | |
|---|---|---|---|---|
| | GM₃ Lactone | | GM₃ | |
| | strong positive (2000 cpm) | weak positive (800–1500 cpm) | strong positive (2000 cpm) | weak positive (800–1500 cpm) |
| Reactivity with GM₃ lactone | 1/192; 5/288*; 2/288* | 23/192 | 0/192 | 5/192 |
| Reactivity with GM₃ | 0/192 | 9/192 | 0/192 | 0/192 |

*Separate experiments based on three 96-well plates. Antibodies from these hybridomas react with both GM₃ and GM₃ lactone after their establishment.

As shown in Table I above, in one experiment, after immunization with GM₃ lactone, 7 strongly positive hybridomas were obtained out of 288 clones screened. On the other hand, no hybridomas were obtained after immunization with native GM₃ and screening of 192 clones. This difference is much greater if the 23 weakly positive hybridomas obtained after immunization with GM₃ lactone are included.

The results in Table I above demonstrate that immunization of mice with GM₃ lactone, but not with native GM₃, elicits many hybridomas secreting monoclonal antibodies. These results demonstrate that GM₃ lactone is a superior immunogen than native GM₃.

One of the monoclonal antibodies established after immunization of mice with GM₃ lactone was designated DH2 antibody. The isotope of this antibody, determined using rabbit anti-mouse IgG antibodies (Miles Biochemical, Elkhart Ind.) was identified as IgG₃. DH2 antibody was saved for further analysis. Hybridoma DH2 has been deposited with the American Type Culture Collection under accession number HB9663.

B Analysis of DH2 Antibody

In order to determine the reactivity of DH2 antibody to GM₃ and GM₃ lactone, the following experiments were carried out.

20 pmole of GM₃ (·) or GM₃ lactone (○) was added along with 50 ng PC and 30 ng cholesterol, dissolved in ethanol, per well of 96-well polyvinyl plastic plates and dried (see FIG. 2A) or 20 pmole of GM₃ (·) or GM₃ lactone (○) was dissolved in PBS per well of 96-well gelatin-coated polyvinyl plastic plates and dried (see FIG. 2B). The wells were blocked with 5.0% (w/v) bovine serum albumin in PBS for 2 hours and reacted with the various concentrations of DH2 antibody shown in FIG. 2A and 2B for 2 hours at room temperature. After washing, bound antibody was detected using 50 μl of a second antibody (rabbit anti-mouse IgG and IgM antibody (Miles Biochemical, Elkhart, Ind.)) followed by detection with 50 μl of $^{125}$I-Protein A. Finally, the wells were cut and the radioactivity was counted in a gamma counter. The results are shown in FIGS. 2A and 2B.

As shown in FIG. 2B DH2 antibody reacted with GM₃ lactone preferentially, but also reacted with GM₃, when GM₃ lactone and GM₃ were coated on gelatin-coated polyvinyl plastic plates. However, as shown in FIG. 2A, DH2 antibody did not show reactivity with GM₃ lactone dried from an ethanol solution, i.e., only GM₃ strongly reacted with DH2 antibody when dried from an ethanol solution. This property is characteristic of anti-ganglioside antibodies established after immunization with ganglioside lactones i.e., anti-ganglioside lactone antibodies cross-react strongly only with native gangliosides when native gangliosides are coated on either a polyvinyl plastic surface or present on a lipid bi-layer. However, anti-ganglioside lactone antibodies react strongly with both lactones and native gangliosides when coated on gelatin-coated polyvinyl plastic plates. Lactones may have special conformation, which causes them to adhere on a polyvinyl plastic surface through their hydrophobic epitope. Therefore, lactones directly coated on a polyvinyl plastic surface show a very weak reactivity with specific antibodies, whereas lactones do not adhere on gelatin through the hydrophobic epitope but, rather, interact through the ceramide moiety. Thus, it is necessary, that lactones be presented on gelatin-coated polyvinyl plastic plates in order to demonstrate their reactivity.

In order to determine the reactivity of DH2 antibody to glycolipids other than GM₃ or GM₃ lactone, the following experiments were carried out.

20 pmole of each of the glycolipids shown in FIG. 3 were added separately along with 50 ng PC and 30 ng cholesterol, dissolved in ethanol, per well of 96-well polyvinyl plastic plates and dried. The binding of DH2 antibody to the wells was carried out as described above. The results are shown in FIG. 3.

As shown in FIG. 3 DH2 antibody reacted strongly with GM₃ containing N-acetyl-neuraminic acid NeuAcGM₃ (·)), but only weakly with GM₃ containing N-glycolyl-neuraminic acid (NeuGcGM₃) (○) or sialylparagloboside (SPG ( )). Also as shown in FIG. 3, DH2 antibody did not react with the other glycolipids tested i.e., GM₁, GD1a, GD1b, GT1, galactosylceramide and sialyllactonorhexaosylceramide (□).

The specificity of DH2 antibody for glycolipids was further determined by thin layer chromatography immunostaining on Baker s thin layer chromatography plates (J. T. Baker Chemical Co., Phillipsburg, N.J.) using a slightly modified version of the procedure described by Magnani, J. L. et al, Anal. Biochem., 109:399–402 (1980). More specifically, glycolipids were applied on the thin layer chromatography plates using a solvent system of chloroform:methanol:water ((50:40:10) (v/v/v)) containing 0.05% (w/v) CaCl₂. After drying, the thin layer chromatography plates were blocked for 2 hours with 5.0% (w/v) bovine serum albumin in PBS and reacted by immersion in DH2 hybridoma culture supernatant at room temperature overnight. After washing, bound antibody was detected using 50 μl of a second antibody (rabbit anti-mouse IgG antibody (Miles Biochemical, Elkhart, Ind.)), followed by detection with 50 μl of $^{125}$I-Protein A. The thin layer chromatography plates were assayed by autoradiography. The results are shown in Table II below.

TABLE II

Specificity of DH2 Antibody for Glycolipids Determined by Thin Layer Chromatography Immunostaining

| Glycolipid | Reactivity |
|---|---|
| NeuAcGM$_3$ (dog erythrocytes) | + |
| NeuAcGM$_3$ (B16 melanoma) | + |
| NeuAcGM$_3$ (rat brain) | + |
| NeuAcGM$_3$ lactone (dog erythrocytes) | + |
| NeuGcGM$_3$ | − |
| NeuGcGM$_3$ lactone | − |
| Sialylparagloboside | ± |
| Sialylparagloboside lactone | − |
| Sialyllactonorhexaosylceramide | − |
| Sialyllactonorhexaosylceramide lactone | − |
| NeuAcGM$_3$ ethylester | − |
| NeuAcGM$_3$ gangliosidol | − |
| GM$_2$ | − |
| GM$_1$ | − |
| GM$_1$ lactone | − |
| GD1a | − |
| GD1b | − |
| GD1b lactone | − |
| GT1 | − |
| Asialo GM$_2$ | − |
| Lactosylceramide | − |
| Glucosylceramide | − |

+, positive reactivity
±, weak positive reactivity
−, negative reactivity

As shown in Table II above, DH2 antibody reacted strongly only with GM$_3$, which contains N-acetylneuraminic acid (NeuAc), and its lactone, not with any of the other glycolipids tested. Further, weak staining was observed with SPG, but the lactone of SPG was not reactive. It is noteworthy that GM$_3$ ethylester (NeuAcGM$_3$ ethylester) and the reduced form of GM$_3$, in which the carboxyl group of the sialic acid was reduced to alcohol (NeuAcGM$_3$ gangliosidol), were not reactive. NeuAcGM$_3$ gangliosidol has no carboxyl group. Instead it has a hydroxyl group at the C-1 position of the sialic acid. Thus, it has an entirely different conformational structure from GM$_3$ and cannot be converted into a lactone. Further, since various types of lactones derived from other gangliosides, such as lactones of SPG, sialyllactonorhexaosylceramide, GM$_1$, and GD1b were all negative, DH2 antibody reactivity to lactone was limited to that of N-acetyl GM$_3$. These results demonstrate that DH2 antibody reacts with both GM$_3$ and GM$_3$ lactone but, not with other types of gangliosides or other lactones. These results also demonstrate that DH2 antibody shows preferential reactivity with GM$_3$ lactone under certain conditions, i.e., when the GM$_3$ lactone is dried on a gelatin or BSA coated polyvinyl plastic surface, and preferential reactivity with GM$_3$ under other conditions, i.e., when the GM$_3$ lactone is directly dried from an ethanol solution on a polyvinyl plastic surface.

In order to compare the reactivity of DH2 antibody to various cell lines in comparison with that of M2590 antibody, an IgM monoclonal antibody established after immunization of C57BL/6 mice with B16 melanoma cells as described in Taniguchi, M., *Jpn. J. Cancer Chemother.*, 75:413-426 (1984), the following experiments were carried out.

Various myeloma and other tumor cell lines shown in Table III below were harvested using 0.2% (w/v) EDTA and 0.2% (w/v) trypsin, washed with PBS and incubated with 20 μg/ml of DH2 antibody or 10 μg/ml of M2590 antibody, as first antibodies, for 1 hour in ice. After several washes with ice cold PBS, the cell lines were incubated with 50 μl of fluorescein-labeled goat anti-mouse IgG+IgM (Miles Biochemical, Elkhart, Ind.) as a second antibody and immuno-fluorescence was analyzed by microscopy, using, as negative control cells, cells which had been incubated with the second antibodies but without the first antibodies. The results are shown in Table III below.

TABLE III

Immunofluorescence Test of Various Cell Lines With DH2 and M2590 Antibodies

| Cell Line | Origin | Reactivity with DH2 | Reactivity with M2590 |
|---|---|---|---|
| B16 | mouse melanoma | +++ | +++ |
| B16F1 | mouse melanoma | +++ | +++ |
| B16F10 | mouse melanoma | +++ | +++ |
| M2669 | human melanoma | + | + |
| M1733 | human melanoma | + | + |
| M2981 | human melanoma | − | ± |
| M2291 | human melanoma | − | ND |
| P36-F4 | human melanoma | + | − |
| HMV-I491B10 | human melanoma | − | − |
| FM3A/LF28-7 | mouse breast carcinoma | − | − |
| FUA169 | mouse breast carcinoma | ++ | ++ |
| HTB19 | human lung carcinoma | ± | ND |
| A431 | human epidermoid carcinoma | − | − |
| SW403 | human colon carcinoma | − | − |
| MKN45 | human gastric carcinoma | − | − |
| K562 | human erythroleukemia | − | ND |
| A-204 | human rhabdomyoscarcoma | − | − |
| BHK | hamster fibroblasts | ± | + |
| NRK | rat fibroblasts | + | + |
| FRE | rat fibroblasts | + | + |
| dog erythrocytes | | +++ | +++ |
| rabbit erythrocytes | | − | − |
| human erythrocytes | | − | − |

+++, almost 100% of the cells were positive; ++, more than 50% of the cells were positive; +, less than 50% of the cells were positive; ±, less than 1% of the cells were positive; −, negative; ND, not determined.

As shown in Table III above, those cells showing strong immunofluorescence with DH2 antibody and M2590 antibody were B16 mouse melanoma and its variants, mouse breast carcinoma FUA169 and dog erythrocytes. All of these highly reactive cells have been characterized by a relatively high concentration of GM$_3$. On the other hand, as shown in Table III above, normal cells or non-melanoma cells, which contain a relatively low concentration of GM$_3$, did not react with DH2 antibody. These results demonstrate that DH2 antibody can recognize the density of GM$_3$ organized in the cell surface membrane, i.e., DH2 antibody can only react with GM$_3$ at densities higher than a threshold value of about 10-15 mol %. In this respect, DH2 antibody's specificity is similar to that of M2590 antibody.

EXAMPLE 2

Effective DH2 Antibody on B16 Melanoma Cell Growth In Vitro and In Vivo

A. In Vitro Study

To study the effect of DH2 antibody on B16 melanoma cell growth in vitro, B16 melanoma cells were harvested with 0.2% (w/v) EDTA and 0.2% (w/v) trypsin and placed in 24 well culture plates (Becton-Dickinson, Oxnard, Calif.) at a density of $5 \times 10^4$ cells/well and grown in RPMI medium supplemented with 3.0% (v/v) fetal calf serum at 37° C. After 24 hours and 48 hours, 50 μg/ml of DH2 antibody (·); 50 μg/ml of M2590 antibody ( ), which, as discussed above, is an IgM antibody which is also directed to GM$_3$ and GM$_3$ lactone; 50 μg/ml of CU-1 anti-Tn ( ), which is an IgG$_3$ antibody which reacts with Tn-antigens; or PBS for control (○) was added. The number of cells were counted at 24 hours, 43 hours, 55 hours and 72 hours after the beginning of culturing. The results are shown in FIG. 4.

As shown in FIG. 4, cell growth of B16 melanoma was greatly inhibited by the presence of DH2 antibody when compared to M2590 antibody and CU-1 anti-Tn. In a similar experiment, using human colonic carcinoma cell line SW403 which does not express $GM_3$, inhibition of human colonic carcinoma cell growth was not observed using DH2 antibody. These results demonstrate that DH2 antibody, originally raised after immunization with $GM_3$ lactone, is capable of inhibiting melanoma growth in vitro.

Furthermore, as shown in FIG. 5, wherein the effects of the following concentrations of DH2 antibody on B16 melanoma cell growth in vitro was ascertained: 100 μg/ml (·); 50 μg/ml ( ); 25 μg/ml (○); and 12.5 μg/ml (Δ); and PBS as a control (□) was carried out as described above, the cell growth inhibition induced by DH2 antibody is dose-dependent, i.e., clear inhibition is only observed at high concentrations of antibody (50-100 μg/ml).

The inhibition of B16 melanoma cell growth caused by DH2 antibody can be reversed if the cells are exposed to normal media without DH2 antibody.

B. In Vivo Study

To study the effect of DH2 antibody on B16 melanoma cell growth in vivo, two groups of four C57BL/6 mice were given subcutaneous injections of $5 \times 10^6$ cells of B16 melanoma at each of two separated sites on the back (day 0). On days 0, 2, 4, 6, 8, 10, 12 and 14 experimental group animals were injected with 4.0 μg of DH2 antibody in 400 μl of PBS via the tail vein. Control group animals were injected with 400 μl of PBS on the same day. Three diameters ($d_1$, $d_2$ and $d_3$) of the tumors were measured and the tumor volumes were calculated by the formula $(\pi/2)(d_1, d_2, d_3)$. The results are shown in FIGS. 6A and 6B.

As shown in FIG. 6A DH2 antibody exhibits significant growth inhibition of B16 melanoma cells in vivo. More specifically, in 2 out of the 8 cases of B16 melanoma cells in mice, B16 melanoma cell growth was almost completely inhibited until day 25. Control animals, shown in FIG. 6B, all died before day 20. The average life-span of B16 melanoma-bearing mice treated with DH2 antibody was 22.5 days, while that of control animals was 12.5 days.

DH2 antibody distribution was determined in B16 melanoma-bearing mice after injection of $^{125}$I-labeled antibody. More specifically, three C57BL/6 mice were injected with $5 \times 10^6$ B16 melanoma cells subcutaneously. Drinking water for the mice was changed to 0.1% (w/v) KI 5 days before DH2 antibody injection. 10 days after B16 melanoma cell innoculation, 20 μg (60 μCi) of $^{125}$I-labeled-DH2 antibody prepared using IODO-BEADS (Pierce Chemical Rockford, Ill.) were injected via the tail vein and mice were sacrificed 72 hours later. After taking a blood sample from the cardiac cavity, PBS was injected into the heart to flush blood from the tissues. Samples from tissues and tumors were weighed and the radioactivity was counted in a gamma counter. The in vivo tissue distribution was expressed as a ratio of radioactivity in tumor to normal tissues (cpm/g in tumor tissue)/(cpm/g in normal tissue)). The results are shown in Table IV below.

TABLE IV

Distribution of $^{125}$I-labeled DH2 Antibody in Tissues of B16 Melanoma Bearing Mice

| Organ or Tissue | (cpm/g of tumor tissue)/ (cpm/g of normal tissue) (mean value from triplicate experiments) |
|---|---|
| Blood | 1.04 |
| Bone marrow | 42.00 |
| Thymus | 14.10 |
| Spleen | 10.00 |
| Skin | 5.55 |
| Muscle | 13.51 |
| Bone | 14.62 |
| Heart muscle | 7.81 |
| Thyroid and adjacent tissue | 6.11 |
| Lung | 4.79 |
| Liver | 14.53 |
| Kidney | 4.13 |
| Intestine | 12.32 |
| Intestinal mesentery | 14.21 |
| Brain | 90.60 |
| Urinary bladder | 3.94 |
| Uterus and attached tissue | 4.44 |

As shown in Table IV above, the highest level of activity was observed in the original melanomas subcutaneously grown and in blood samples, followed by urogenital tissue. The lowest activity was found in bone marrow and the brain. These results demonstrate that DH2 antibody strongly binds to melanoma cells in vivo as well as to blood, although other tissues and organs showed much less binding activity than the melanoma cells.

EXAMPLE 3

Cytotoxicity Induced by DH2 Antibody

The effects of DH2 antibody on antibody-dependent cytotoxicity was studied using the 4 hour chromium assay described by Grabstein K. In *Selected Release Methods of Cellular Immunology*, Mishell, B. B. et al, Eds., pages 124–137, Freeman & Co., San Francisco (1980). More specifically, mononuclear cells from peripheral blood from healthy human donors prepared by Ficoll-Paque (Pharmacia Piscataway, N.J.) or lymphocytes harvested from spleens of C57BL/6 mice, were used as effector cells. $1.0 \times 10^6$ B16 melanoma cells were used as target cells and labeled for 2 hours with 100 μCi sodium ($^{51}$Cr) chromate in RPMI medium supplemented with 3.0% (v/v) fetal calf serum at 37° C. in a $CO_2$ incubator, washed, incubated with 50 μg/ml of DH2 antibody in RPMI medium supplemented with 3.0% (v/v) fetal calf serum for 30 min at 37° C. in a $CO_2$ incubator and washed again. $^{51}$Cr-labeled B16 melanoma cells treated with DH2 antibody were placed in 96-well round bottom plate (Costar, Cambridge, Mass.) at a density of $5 \times 10^3$ cells/well and incubated with various concentrations of effector cells as shown in Table V below for 4 hours at 37° C. The plates were then centrifuged at 500×g for 5 min and the radioactivity was measured in a 125 μl aliquot of each supernatant using a gamma counter.

Spontaneous $^{51}$Cr release was determined in wells that contained only labeled B16 melanoma cells treated with DH2 antibody for 24 hours.

Total release was determined using the supernatant of the wells in which the cells were lysed with 2.0% (v/v) Triton X-100 and centrifuged. The percentage of lysis was calculated as follows:

$$\frac{\text{(Experimental release)} - \text{(Spontaneous release)}}{\text{(Total release)} - \text{(Spontaneous release)}} \times 100$$

The results are shown in Table V below.

TABLE V

| Antibody-dependent Cytotoxicity of DH2 Antibody Against B16 Melanoma Cells | | | | | | | |
|---|---|---|---|---|---|---|---|
| Human effector cells | | | | C57BL/6 mouse effector cells | | | |
| Effector: target ratio | 200 | 100 | 50 | 25 | 200 | 100 | 50 | 25 |
| Percentage of lysis | 20.3 | 7.0 | 0 | 0 | 12.3 | 6.3 | 2.9 | 5.3 |

As Table V above clearly demonstrates, antibody-dependent cytotoxicity was demonstrated by a lysis of the target cells at high effector:target ratio. This lysis was observed with both human and mouse effector cells. The release of $^{51}$Cr observed in this experiment was found to be due to lysis of target cells by cytotoxic effector cells since DH2 antibody alone did not cause significant release of $^{51}$Cr under the same conditions i.e., release of $^{51}$Cr by DH2 antibody alone during 24 hours was only 3.0%. These results demonstrate that DH2 antibody shows a clear antibody-dependent cytotoxic effect on melanoma cells.

EXAMPLE 4

Active Immunization With GM$_3$ Lactone

In order to determine the effect on B16 melanoma cell growth by active immunization of mice with GM$_3$ lactone or GM$_3$ coated on acid-treated *Salmonella minnesota* the following experiments were carried out.

10 BALB/c mice were immunized with native GM$_3$ or GM$_3$ lactone coated on acid-treated *Salmonella minnesota* as described above Immunization was carried out by intravenous injection of 200 μl of the GM$_3$ or GM$_3$ lactone preparation once per week for 4 weeks. Subsequently, $1.0 \times 10^5$ B16 melanoma cells of clones F-1 or F-10, were subcutaneously injected into the back of the mice and tumor growth was observed after 20 days. As controls, other glycolipids, such as paragloboside coated on acid-treated *Salmonella minnesota*, and *Salmonella minnesota* alone, were used in the same amounts as discussed above. The results are shown in Table VI below.

TABLE VI

| Effect of Immunization With GM$_3$ Lactone on B16 Melanoma Development | | | |
|---|---|---|---|
| Melanoma B16 | *Salmonella minnesota* alone | GM$_3$ Adsorbed on *Salmonella minnesota* | GM$_3$ Lactone Adsorbed on *Salmonella minnesota* |
| F-1 | 10/10 | 10/10 | 2/10 |
| F-10 | 10/10 | 10/10 | 3/10 |

In Table VI above, the numbers indicate the number of animals which died over the total number of animals immunized. The results in Table VI above demonstrate that tumor growth was reduced in the group immunized with GM$_3$ lactone but not in the group immunized with GM$_3$ or with other glycolipids, such as paragloboside coated on *Salmonella minnesota*, or with *Salmonella minnesota* alone. These results demonstrate that GM$_3$ lactone but not GM$_3$ is capable of suppressing tumor growth in vivo.

While the invention has been described in detail and with reference to specific embodiments thereof, it will be apparent to one skilled in the art that various changes and modifications can be made therein without departing from the spirit and scope thereof.

We claim:

1. A method for inducing an immune response to a tumor-associated ganglioside comprising administering to a subject a composition consisting essentially of:
   (a) an immunogenically effective amount of an isolated lactone of a tumor-associated ganglioside; and
   (b) a pharmaceutically acceptable carrier.

2. The method as claimed in claim 1, wherein said tumor-associated ganglioside is selected from the group consisting of GD$_3$, GD$_2$, sialyl Le$^a$, sialyl Le$^X$, sialyl difucosyl Le$^x$, GM3, 6C ganglioside, G2 ganglioside, disialosyl Le$^a$, monosialyl type 1 chain, disialosyl type 1 chain and fucosyl GM$_1$.

3. The method as claimed in claim 1, wherein said immunogenic effective amount is about 2.0 to 5.0 μadsorbed on about 20 to 100 μg of carrier.

4. The method as claimed in claim 1, wherein said carrier is selected from the group consisting of Bacillus Calmette-Guerin (BCG), diptheria toxoid, and tetanus toxoid.

5. The method as claimed in claim 1, wherein said carrier is an artificial or natural membrane or vaccinia virus.

* * * * *